United States Patent [19]

Charette et al.

[11] Patent Number: 5,416,007
[45] Date of Patent: * May 16, 1995

[54] ENHANCED PROTEOLYTIC CLEAVAGE OF RECOMBINANT FUSION PROTEINS

[75] Inventors: Marc F. Charette, West Roxbury; Roberto Crea, Boston; Charles M. Cohen, Medway, all of Mass.

[73] Assignee: Creative BioMolecules, Inc., Hopkinton, Mass.

[ * ] Notice: The portion of the term of this patent subsequent to May 7, 2008 has been disclaimed.

[21] Appl. No.: 273,870

[22] Filed: Jul. 12, 1994

Related U.S. Application Data

[63] Continuation of Ser. No. 899,237, Jun. 16, 1992, abandoned, which is a continuation of Ser. No. 746,281, Sep. 2, 1991, abandoned, which is a continuation of Ser. No. 28,483, Mar. 20, 1987, abandoned.

[51] Int. Cl.$^6$ .................... C12P 21/06; C12N 11/12; C12N 11/06; C12N 11/08
[52] U.S. Cl. ................................ 435/68.1; 435/69.7; 435/176; 435/177; 435/178; 435/179; 435/180; 435/181; 530/407; 935/47; 935/51
[58] Field of Search ................. 435/69.1, 69.7, 68.1, 435/176, 177, 178, 179, 180, 181; 530/407; 935/47, 51

[56] References Cited

U.S. PATENT DOCUMENTS

| | | | |
|---|---|---|---|
| 4,352,884 | 10/1982 | Nakashima et al. | 435/180 |
| 4,366,246 | 12/1982 | Riggs | 435/68 |
| 4,425,437 | 12/1984 | Riggs | 435/317 |
| 4,431,739 | 2/1984 | Riggs | 435/253 |
| 4,443,540 | 4/1984 | Chervan et al. | 435/69 |
| 4,511,502 | 4/1985 | Builder et al. | 530/427 |
| 4,543,329 | 9/1985 | Daum | 435/69 |
| 4,563,424 | 1/1986 | Riggs | 435/71 |
| 4,694,035 | 9/1987 | Kasai et al. | 524/458 |
| 4,743,679 | 5/1988 | Cohen et al. | 530/350 |
| 5,013,653 | 5/1991 | Huston et al. | 435/69.7 |

FOREIGN PATENT DOCUMENTS 0035384 9/1981 European Pat. Off.

OTHER PUBLICATIONS

Sassenfeld and Brewer, "A polypeptide fusion designed for the purification of recombinant proteins". Biotech. (1984) 76–81.

Nagai and Thogersen, "Generation of B-globin by sequence-specific proteolysis of a hybrid protein produced in *Escherichia coli.*" Nature (1984) 309:810–812.

Germino et al., Proc. Natl. Acad. Sci. USA, vol. 81, pp. 4692–4696, 1984; "Rapid Purification of a cloned gene . . .".

McCaman et al., J. Biol. Chem., vol. 261 (33), pp. 15345–15348, 1986; "A Mutated Bovine Prochymosin . . .".

Brewer and Sassenfeld, "The purification of recombinant proteins using C-terminal polyargineni fusions." Trends in Biotech. (1985) 3:119–122.

Uhlen et al, "Gene fusion vectors based on the gene for staphylococcal protein A." Gene. (1983) 23:369–378.

Germino et al, "Use of gene fusions and protein—protein interaction in the isolation of a biologically active regulatory protein: The replication initiator protein of plasmid R6K". Proc. Natl. Acad. Sci. USA. (1983) 80:6848–6852.

*Primary Examiner*—Robert A. Wax
*Assistant Examiner*—Keith D. Hendricks
*Attorney, Agent, or Firm*—Testa, Hurwitz & Thibeault

[57] ABSTRACT

Disclosed are methods for increasing the yield of intact target proteins by cleaving fused polypeptides made by recombinant DNA techniques. The fused polypeptides are designed at the DNA level to have a preselected primary cleavage site in a pendant polypeptide fused to a protein of interest. Structural features of the fused polypeptide and cleavage reaction environment are controlled to favor cleavage by a preselected cleavage agent at the primary cleavage site over a second cleavage agent-sensitive amino acid sequence in the target protein. The cleavage reaction is terminated before completion when the ratio of intact target protein to truncated, cleaved target protein is optimized, and the remaining reaction mixture comprising uncleaved fused polypeptide is resubjected to the cleavage agent. The presence of charged organic molecules in the cleavage reaction mixture favors cleavage at the primary cleavage site. The endopeptidase used for cleavage may be immobilized on an insoluble support matrix.

29 Claims, 5 Drawing Sheets

ENHANCED PROTEOLYTIC CLEAVAGE OF RECOMBINANT FUSION PROTEINS

This is a continuation of application Ser. No. 07/899,237, filed Jun. 16, 1992, now abandoned, which is a continuation of Ser. No. 07/746,281, filed Sep. 2, 1991, now abandoned, which is a continuation of Ser. No. 07/028,483, filed Mar. 20, 1987, now abandoned.

This invention relates to the isolation and purification of polypeptides produced using genetic engineering techniques. More particularly, it relates to a method of improving the yield of intact target protein produced by cleaving a fused recombinant polypeptide expressed by a transformant.

Advancements in recombinant DNA technology permitting foreign genes to be incorporated into various cells have made possible the expression of a product foreign to the cell. The molecular biology governing the expression of recombinant DNA places a variety of constraints on the form of polypeptides or proteins produced in the host organism. For instance, intracellular enzymes often will degrade the protein of interest, and separation of this protein from other materials expressed by or comprising the structural materials of the host organism may be difficult.

The development of fusion or hybrid polypeptide methodology has facilitated the protection, isolation, and purification of genetically engineered polypeptides and overcomes some of the constraints described above. Protection from intracellular degradation can be accomplished by fusing a sequence of amino acids to the target protein to avoid digestion by enzymes within the cell. The fusion protein is encoded by an engineered DNA sequence comprising the gene coding for the protein of interest and the sequence of a polypeptide other than the protein of interest. A fusion product can be secreted from the host into the growth medium by fusing a signal peptide to the target. In addition, the hybrid can be designed to facilitate isolation and purification if the target protein is fused to a polypeptide having characteristics exploitable in purification.

Fusion methodology has been discussed at length in the prior art. For example, European Patent Application No. 0047600 is understood to disclose a process for synthesizing bovine growth hormone by producing a fusion protein and purifying the growth hormone from the culture medium of the host organism. Other proteins have been produced through fusion techniques.

Generally, the prior art teaches that genetic material encoding a cleavage site can be incorporated between the DNA encoding the desired protein and the DNA encoding the additional fused material. Expression yields a precursor protein comprising the amino acid sequence of the target polypeptide linked to one or more amino acids defining a selected cleavage site and another amino acid sequence. EPO 0035384 discloses the use of fusion proteins having specific cleavage sites incorporated in their structures which facilitate purification of expression products. EPO 0161937 discloses a recombinant fusion protein including a DNA sequence encoding a site specifically cleavable by blood coagulation Factor Xa. EPO 0163573 is understood to disclose a nucleotide sequence inserted into a plasmid expression vector which codes for an amino acid sequence specifically recognizable by the proteolytic enzyme renin.

The fusion product can comprise a moiety which facilitates isolation of the desired product. See, e.g., PCT/84/03103. U.S. Pat. No. 4,431,739 also describes a method of expressing a precursor protein containing a desired protein, an additional polypeptide, and a selective cleavage site adjacent the desired protein.

The production of proteins with fusion methodology is also faced with constraints. Efficient cleavage of the fused material to obtain purified target protein can be difficult to achieve. Often only some fraction of the fusion protein is properly cleaved, and therefore existing methods provide low purification efficiency. Furthermore, the cleavage agent may cleave at several locations resulting in product loss and the production of contaminating fragments.

What is needed is a method for increasing the yield of the purified proteins made using fusion technology. A general method of cleaving fused polypeptides which enables recovery of increased quantities of intact target protein could promote significantly the commercial availability of proteins produced by recombinant DNA techniques.

It is an object of this invention to provide an improved procedure for cleaving genetically engineered (recombinant) fused polypeptides. Another object is to provide a method for obtaining recombinant protein of interest in improved yields. Another object is to provide a method which can be adapted to any polypeptide of interest which can be coded for and expressed by a host organism. Still another object is to provide such a procedure which is both efficient and inexpensive.

These and other objects of the invention will be apparent from the description, drawing, and claims that follow.

SUMMARY OF THE INVENTION

This invention provides processes for cleaving recombinant fused polypeptides to obtain enhanced quantities of intact cleaved target protein. The invention is useful in cleaving fused polypeptides which comprise a sequence of amino acids defining a pendant polypeptide (either a leader or trailer sequence) linked to a target protein, and having one or a sequence of amino acids adjacent the target protein which serves as a site of reaction for a selected cleavage agent such as an endopeptidase.

As disclosed hereinafter, many cleavage agents are known which, under appropriate reaction conditions, cleave a protein by hydrolysis of a peptide bond preferentially at some specific cleavage site adjacent one or a sequence of specific amino acids. The problem is that the amino acid or amino acid sequence constituting the cleavage site is also often present in the sequence of the target protein, or the target protein contains a sequence which also is sensitive to the cleavage agent. Thus, upon exposure to the cleavage agent, a reaction occurs which separates the target protein from the pendant polypeptide, but also a second, counterproductive cleavage reaction occurs in which the target protein is cleaved. As disclosed, for example, in copending application Ser. No. 028,484 one methodology which potentially can eliminate cleavage of the target protein is to substitute a heterologous amino acid or amino acid sequence for those constituting the cleavage site in the target protein, preferably by engineering the DNA. However, this strategy may affect adversely the bioproperties of the target protein or modify the protein's structure sufficiently to stimulate an immune reaction when the protein is used in vivo.

In accordance with this invention, it has been discovered that fused polypeptides having a primary cleavage site defined by an amino acid or amino acid sequence adjacent the target protein, and in addition having a secondary reactive cleavage site in the structure of the target protein, can be subjected to a cleavage protocol which produces enhanced quantities of intact, cleaved target protein. The fused polypeptide is subjected to a cleavage agent in a reaction mixture under conditions in which the cleavage agent cleaves the fused polypeptide at the primary cleavage site at an initial reaction rate which is greater than the rate of cleavage at the secondary cleavage site. As the desired primary product accumulates, the rate of cleavage at the secondary site approaches the rate of cleavage at the primary site. Eventually the reaction reaches a point at which the net accumulation of primary product stops since the primary product is degraded to the secondary product as soon as it is produced. Various strategies disclosed herein permit enhancement of this differential cleavage reaction rate.

In accordance with the invention, intact target protein or primary product is removed from the reaction mixture prior to the differential cleavage reaction reaching equilibrium, thereby producing a first yield of target protein. The remaining reaction mixture is then resubjected to the cleavage agent to produce additional amounts of cleaved intact target protein, and these steps are repeated as often as is economically practical. This "recycle method" results in an overall yield of intact target protein significantly greater than the yield attained, for example, when the cleavage reaction is simply left to go to completion.

The cleavage reaction preferably is conducted while the target protein is disposed in its renatured, tertiary conformation. When the target protein comprises two or more cysteine residues, the cleavage may be conducted under oxidizing conditions so that the target protein maintains its tertiary conformation by disulfide bonding. The tertiary conformation of the target protein often sterically hinders access of an endoprotease to a cleavage site in the target protein structure, resulting in preferential cleavage at the primary cleavage site. Often, a pH can be selected which favors cleavage at the primary cleavage site. The pendant polypeptide can itself be engineered to favor endoproteolytic cleavage at the primary cleavage site by the use of a "hinge region" comprising an amino acid sequence disposed about the primary cleavage site having the properties described hereinafter. Also, it has been discovered that differential cleavage reaction rates can often be promoted by conducting the cleavage reaction in the presence of certain organic ions.

The invention may be practiced with a variety of cleavage agent/cleavage site pairings as discussed below. The currently preferred cleavage agent/cleavage site pairing is *Staphylococcus aureus* V-8 protease (V-8 protease) which cleaves on the carboxyl side of a glutamic acid residue.

In one important aspect of the process of the invention, the endoprotease may be immobilized on a support matrix and the cleavage reaction conducted by passing a solution containing the fused polypeptide over the support matrix. The time the fused polypeptide remains in reactive contact with the immobilized endopeptidase can be controlled so as to favor cleavage of the fused polypeptide at the primary cleavage site.

While the invention can be used to produce a large number of different target proteins, it has been developed most thoroughly in its application to the production of epidermal growth factor (EGF) produced as a fusion protein by recombinant DNA methods. The fusion protein comprises a glutamic acid residue as the primary cleavage site, and V-8 protease as the selected cleavage agent. Human EGF is a 53 amino acid protein containing four glutamic acid residues. If, as preferred, the cleavage reaction is conducted under oxidizing conditions so that the protein is held in its native conformation by disulfide bonds, only the Glu 51 residue is attacked to any significant extent by V-8 protease. Preferential cleavage at the built in cleavage site adjacent the EGF is further promoted by including in the reaction mixture during cleavage an organic molecule, preferably one having 12 carbon atoms attached to a charged moiety. The charged molecule may be, for example, a dodecyl sulfate salt, a lauric acid salt, or a zwitterion such as an N-dodecyl, N-lower alkyl sulfonic acid quaternary ammonium zwitterion.

The currently preferred method of separating the cleaved intact target protein from the remaining fusion polypeptide is by differential precipitation.

Other features and embodiments of the invention will be apparent from the following description and claims.

DESCRIPTION

The production of various proteins of interest has heretofore been achieved by expressing fused protein which is collected, purified, and then cleaved to remove the extraneous portion of the molecule. This invention constitutes an improvement and unobvious refinement of the cleavage step of this method. In the practice of the invention, generally, one engineers a recombinant DNA which, upon expression in a suitable host, produces a fused polypeptide. The fused polypeptide preferably is designed to be cleaved efficiently by virtue of its structural properties and/or the cleavage reaction conditions as discussed below. The fused polypeptide may also include a polypeptide moiety in its leader designed specifically to faciliate its purification. Practice of the enhanced cleavage process of the invention enables one to improve the yield of intact protein of interest.

Figure 1:
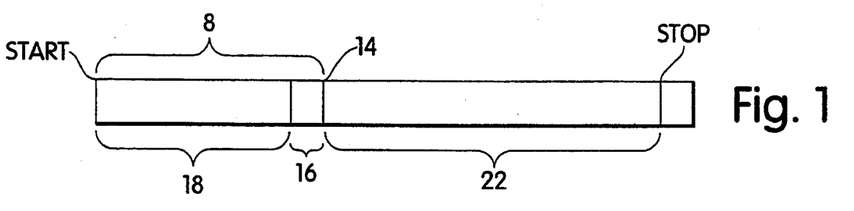
FIG. 1 is a schematic representation of a recombinant DNA encoding a cleavage site, a "hinge region", and a leader sequence, linked to DNA encoding a target protein.
Figure 2:
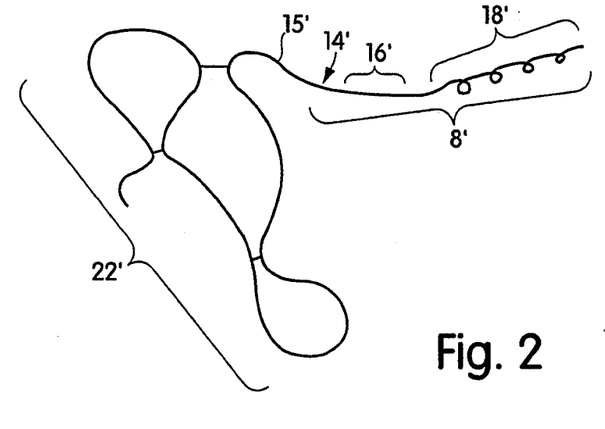
FIG. 2 is a schematic representation of a precursor fused polypeptide of the type used in the practice of the invention. It comprises a cleavage site, a hinge region, and a leader polypeptide, bound to a target protein.

The preferred DNA sequence for the practice of the invention is illustrated in FIG. 1. The protein encoded by the DNA of FIG. 1 is illustrated in FIG. 2, with amino acid sequences synthesized from the DNA regions identified by corresponding primed referenced characters. The DNA is composed of two distinct segments linked together. The segment 8 encodes an amino acid sequence most or all of which will ultimately be discarded (pendent polypeptide). Linked to the DNA coding for the N- or C-terminus of segment 8 is DNA encoding a target protein 22, the protein of interest, which ultimately will be harvested. The DNA segment 8 contains nucleotides preferably encoding three segments: a leader sequence 18, a sequence referred to herein as a "hinge" or "hinge region" 16, and an amino acid or amino acid sequence defining a primary cleavage site 14. The leader sequence may be a known sequence. Its primary function is to achieve high expression of the fused polypeptide in accordance with the generally known fusion protein methodology of the prior art. The leader sequence 18' may also comprise a binding site designed to bind to a preselected receptor to facilitate purification, and/or to have a polypeptide structure designed to promote formation of inclusion bodies within the host cell, or to have an affinity for charged or hydrophobic media. The function of the hinge region 16' is to improve the rate and/or the specificity of the cleavage reaction at the primary cleavage site 14. The primary cleavage site 14' is engineered into the protein by engineering the DNA. Its function is to serve as a site of action for a preselected cleavage agent.

When primary cleavage site 14' comprises a unique amino acid or amino acid sequence in the fused polypeptide, and a cleavage agent having that single specific site of action is employed, one simply permits the cleavage reaction to go to completion. The target protein remains unaffected by the cleavage agent as it contains no cleavage sites.

However, many known cleavage agents have primary and secondary sites of specificity, and often the target protein will contain one or a sequence of amino acids identical to the primary cleavage site 14' or differing amino acid sequences which also are secondarily attacked by the cleavage agent. In these situations, cleavage can occur not only at primary cleavage site 14' as desired, but also at one or more locations in the target protein depicted in FIG. 2 as 15', herein referred to as a secondary cleavage site. This second cleavage reaction reduces target protein yield as some fraction of the target protein is itself cleaved. In accordance with the invention, the yield of intact target protein can be significantly improved in this circumstance by exploitation of the procedures set forth below.

In accordance with the invention, cleavage is conducted under conditions in which the rate of reaction at the primary cleavage site 14' is greater than the rate at the secondary cleavage site 15'. There are several strategies, useful singly or in combination, for attaining this goal.

First, the structure of the fused protein may be designed, typically at the DNA level, such that cleavage at the primary site is enhanced as compared with other potential cleavage sites in the molecule. This is accomplished by engineering a hinge region into the fused polypeptide's amino acid structure adjacent or about the primary cleavage site as disclosed in more detail below, and in copending U.S. application Ser. No. 028,484, filed on even date herewith, the disclosure of which is incorporated herein by reference.

Second, the cleavage reaction may be conducted after the fused polypeptide has been renatured to assume its native tertiary conformation. In a well designed fused polypeptide, no cysteine residues will be present in the vicinity of the primary cleavage site. Typically the target proteins have multiple cysteine residues which serve by formation of disulfide bonds to hold the amino acid chain in a tertiary conformation. When cleavage is conducted in an environment wherein the target protein is permitted to retain its tertiary structure, or after oxidation so that it includes disulfide bonds between cysteine residues, access of the cleavage agent to a cleavage site in the target protein is often hindered. The hindering effect is particularly marked if the cleavage agent is an endoprotease which itself has a tertiary structure. Thus, cleavage at the primary site is favored.

Third, the pH, ionic character, temperature, and other physical properties of the cleavage reaction mixture often can be chosen to promote selective cleavage at the primary cleavage site or to hinder cleavage at a secondary site in the target protein. The particular conditions vary depending on the cleavage agent/cleavage site pairing in question, on the identity of the target protein, and to some extent, on the structure of the fused protein. The literature contains information on the effect of varying pH, etc. on cleavage specificity and efficiency for many cleavage agent/cleavage site pairings. Conditions may be optimized further empirically.

To optimize the effect of the recycle method of the invention, it is preferred to assess at least indirectly the relative rates of cleavage at the primary and secondary sites to enable selection of a time point in the reaction where the ratio of the concentration of intact target protein to other smaller fragments and remaining uncleaved fused protein is optimized. This can be done empirically by periodically removing samples of a test reaction mixture, terminating the cleavage reaction in the samples by, e.g., reducing temperature, and analyzing the samples for target protein, intact fused polypeptide, and the other cleavage fragments using, e.g. chromatography or electrophoretic techniques. Such studies enable one to decide when, prior to completion, the cleavage reaction should be terminated to maximize yield.

At that time point, the cleavage reaction is terminated, the intact target protein is removed, and then the cleavage reaction is allowed to continue. This sequence of steps may be repeated as often as desired. The number of repeats typically will be determined by economic considerations, as a point will be reached when the value of the amount of target protein product recovered in the next cycle will not justify the cost of its production.

In one aspect of the invention, the cleavage reaction is conducted by exposing the fused polypeptide to the selected cleavage agent in a dynamic system in which the endopeptidase cleavage agent is immobilized on an insoluble support matrix. It has been discovered that by controlling the duration of reactive contact between the fused protein and the immobilized endopeptidase enzyme, cleavage can be optimized to enhance target protein yield.

Enzyme immobilization technology is now well developed, and various methods are available and known to those skilled in the art which can readily be applied to known endopeptidase enzymes to covalently link them to various insoluble media. Examples of difunctional linking reagents include diethylamine, ethyl cellulose, glutaraldehyde, and cyanogen bromide. For a review of the state of the art of enzyme immobilization see Wectall et al, 1986, Science, Vol. 1396–1403. The currently preferred media for use in the practice of this aspect of the invention are Sepharose beads (cross-linked polyglucose) available commercially from Pharmacia, and polyvinylidine fluoride-based polymer substrates available commercially from Millipore Corporation under the tradename Immobilon.

The cleavage reaction can be conducted in a flow-through device such as a column, packed, for example, with Sepharose beads having the preselected cleavage agent adhered to the bead surface. Residence time of contact between the immobilized enzyme and the fused polypeptide to be cleaved is the product of the column volume and the flow rate. The optimal residence time of reactive contact readily can be determined empirically. Too short a time results in low yield of target protein; too long a time results in cleavage of the target protein.

It has also been discovered that charged organic molecules can have a marked influence on the cleavage reaction, and are particularly useful in promoting a differential cleavage rate at two identical cleavage sites in a fused polypeptide. The theoretical explanation for the observed effect produced when a charged organic molecule is present in the reaction mixture together with the cleavage agent and the fused polypeptide is unknown. However, the addition of charged organic molecules (salts or zwitterions) to the cleavage reaction often has the effect of altering the cleavage reaction rate to favor cleavage at the primary cleavage site.

The currently preferred organic molecules for use in the cleavage processes of the invention comprise hydrocarbon chains containing a charged group such as a carboxylic acid group, sulfate or sulfite group, or quaternary ammonium group. Sodium dodecyl sulfate, lauric acid, and quaternary ammonium salts and zwitterions may be used successfuly, and are preferred when V-8 protease is the enzyme of choice. The particular ion used and its concentration may be determined empirically. Less than three percent by weight of the cleavage reaction mixture is generally sufficient.

Either the immobilized enzyme technique or the use of organic ions may be exploited alone to cleave fusion proteins, or used in conjunction with the recyle technique.

When practicing the recycle method using an immobilized enzyme, the duration of the repeated exposures of the fused polypeptide to the immobilized cleavage reagent is controlled by controlling the residence time of reactive contact between the enzyme and its fused polypeptide substrate. When practicing the recycle method in dissolved enzyme systems, the reaction is terminated prior to completion by dilution, altering pH, changing temperature, or altering the ionic character of the solution so that the rate of the cleavage reaction is slowed to negligible levels.

Separation of the cleavage digest fragments from remaining intact fused polypeptide may be conducted by any of a large number of conventional separation techniques including HPLC and other forms of chromatography, including affinity chromatography, or by differential precipitation. Since the molecular weights of the fused polypeptide and the target protein are different, and because the two species typically have very different solubility properties, uncleaved remaining fused polypeptides can be precipitated by changing pH, the nature of the solvent, or its ionic strength, leaving lower molecular weight peptide fragments, including the intact target protein, in solution. Centrifugation then permits isolation of the fused polypeptide, which is then redissolved and resubjected to the cleavage enzyme.

Fused Polypeptide Construction and Design

The design criterion for the fused polypeptide useful in the process of the invention will now be described in greater detail. It should be noted that the following teaching should not be regarded as limiting the invention, but rather constitutes the currently preferred designs which often can optimize target protein yield, simplify its purification, and promote high expression levels. Thus, broadly, the recycle method embodiment of the invention can be practiced on any fused polypeptide which has primary and secondary cleavage sites, a target, and a leading or trailing pendant polypeptide. Furthermore, the immobilized enzyme technique is useful even when only one cleavage site is present in the fused polypeptide.

The processes for manipulating, amplifying, and recombining DNA which encodes amino acid sequences of interest are generally well known in the art, and therefore, not described in detail herein. Methods of identifying and isolating genes encoding proteins of interest, or of constructing such genes, are well understood and developed. These processes are described in the patent and other literature. See, for example, U.S. Pat. No. 4,431,739. In general, the methods involve selecting genetic material coding for amino acids which define the protein according to the genetic code.

Accordingly, the fused DNAs and their corresponding fused polypeptides used in the practice of the invention disclosed herein can be constructed with conventional techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short oligonucleotides, cDNA synthesis techniques, and synthetic probes for isolating genes having a particular function. Various promoter sequences and other regulatory DNA sequences used in achieving expression, and various types of host cells are also known and available. Conventional transfection techniques, and equally conventional techniques for cloning and subcloning DNA are also useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic characteristic that can be used to identify which of a family of cells has successfully incorporated the recombinant DNA of the vector.

Cleavage agents typically perform their function by hydrolysis of peptide bonds. The specificity of cleavage agents is determined by the identity of the amino acids at or near the peptide bond which is hydrolyzed. A given cleavage agent may recognize the bond between two specific amino acids or may recognize a bond following one or a specific sequence of amino acids.

The specificity of many cleavage agents is known. For example, trypsin cleaves at the carboxyl side of an arginine or lysine residue. Cyanogen bromide cleaves at methionine only under certain conditions, whereas pepsin with its broad specificity cleaves at the carboxyl side of most amino acids, preferably tyrosine, tryptophan, leucine, methionine, and phenylalanine. V-8 protease cleaves only at glutamic acid or aspartic acid. Dilute acid cleaves at Asp-Pro linkages. The table set forth below lists various known cleavage agents and their primary (and in some cases secondary) sites of action.

TABLE 1

| Cleavage Agent | Major Site of Action | Other Sites |
|---|---|---|
| Trypsin | Arg, Lys | |
| Chymotrypsin | Trp, Phe, Tyr | Leu, Met, His |
| Elastase | Neutral Aliphatic Residues | |
| Pepsin | Phe, Leu, Trp, | Ala, Gly, Glu |
| Papain | Arg, Lys, Gly | Wide specificity |
| Subtilisin | Aromatic and Aliphatic residues | Various |
| Thermolysin | Amino-linked Bonds of Aliphatic residues | Ala, Phe |
| V-8 protease | Glu | Asp |
| Endoproteinase Arg C (Submaxillaris protease) | Arg | |
| Clostripain | Arg | |
| Thrombin | Arg | |
| Collagenase | X—Gly—Pro | X—Ala—Pro X—Gly—Thr |
| Lysobacter enzymogenes (endoproteinase Lys—C) | Lys | |
| Mysobacter Al-1 Protease | Lys | |
| Armillaria mellea | Lys | |
| Flavobacterium meringosepticum | Pro | |
| Factor Xa | Ile—Glu—Gly—Arg | |
| CNBr | Met | |
| BNPS-skatole | Trp | |
| N-bromosuccinimide | Trp | |
| O-iodosobenzoic acid | Trp | |
| HBr/DMSO | Trp | |
| NTCB | Cys | |
| Sodium metal in liquid ammonia | Pro | |
| Hydroxylamine | Asn—Gly | |
| Dilute acid | Asp—Pro | |

Other cleavage agents are known. Those preferred for use in the inventions are enzymes which cleave primarily at the C-terminal side of the cleavage site residue (for pendant polypeptides attached to the amino side of the target polypeptide) or at the N-terminal side of the cleavage site residue (for pendant polypeptides attached to the carboxyl side of the target polypeptide).

The currently most preferred cleavage agent/cleavage site is V-8 protease/Glu.

As illustrated in the drawing, the cleavage site 14' is interposed between the hinge region 16' and the target protein 22'. While this location is preferred, the cleavage site may lie within the hinge region, that is, amino acid residues serving the function of the hinge may be interposed between the amino acids constituting the protein target 22' and the cleavage site 14' (not illustrated). The cleavage site may also be located within terminal regions of the amino acid sequence of a target protein, and the hinge region disposed immediately adjacent the native polypeptide's amino acid sequence. In this case, cleavage results in a truncated analog of the native polypeptide, and the analog becomes the target protein, as that phrase is used herein. However, if a signal peptidase were used as a cleavage enzyme, the cleavage site would be downstream from its site of specificity. A native polypeptide could result from such cleavage.

A segment of DNA 18 encodes a sequence of amino acid sequence 18' designated herein as a leader sequence which, in addition to its function of limiting intracellular degradation, preferably imparts to the fused polypeptide characteristics useful in purification. This polypeptide moiety has characteristics that simplify the separation of the fused product from other materials. The amino acid sequence of the leader 18' can define a molecule having, for example, particular solubility characteristics, to facilitate separation of the fusion product from other polypeptides produced by the cellular host.

A preferred leader sequence defines an amphiphilic alpha-helical structure which contain both hydrophilic and hydrophobic amino acid residues, and can have an affinity for both polar and nonpolar media, depending on ambient pH. The use of this type of leader promotes formation of insoluble inclusion bodies in host cells which aid in isolation of the product.

Further particulars of this type of leader are disclosed in copending application Ser. No. 028,500, filed on even date herewith, the disclosure of which is incorporated herein by reference. Other types of leader sequences may be used, including many leaders disclosed in the patent and other literature.

As represented in FIGS. 1, and 2, the hinge region 16' is encoded by a DNA segment 16. The hinge 16' is included in the fused protein to promote efficient cleavage at the cleavage site 14' by a selected cleavage agent. The expressed hinge region 16' is preferably a random coil segment adjacent or about the cleavage site 14' comprising at least two amino acids that serve to expose the cleavage site to enzymatic or other digestion. This property of the hinge fosters accessibility of the cleavage site to enzymes or other cleavage reagents in the environment of the cleavage reaction and provides a kinetic advantage for preferential digestion at the amino acid residue(s) constituting the cleavage site.

The amino acid sequence comprising the hinge region can vary widely. The sequence often comprises a flexible polypeptide segment which imparts to the portion of the fused polypeptide about the cleavage site the ability to assume a random coil conformation. The amino acids comprising the hinge are responsible for imparting these properties. The hinge region may contain at least one proline residue and may be free of cysteine residues. The presence of one or more nonpolar proline residues substantially precludes the formation of alpha-helical structure in the hinge region. Cysteine contains a sulfhydryl or thiol group, which forms disulfide linkage readily. Therefore, its presence can work against the desired lack of fixed structure of the hinge region.

Preferably, the hinge region is a polypeptide containing from about two to twenty amino acids.

Particularly when the preselected cleavage agent is an endopeptidase, it is important that the hinge region be soluble in aqueous environments. Amino acids having charged side groups and hydrophilic properties thus may be included in the hinge to promote solubility. These include the anionic residues Glu and Asp, the cationic residues Arg and Lys, and the neutral hydrophilic residues Ser and Thr.

One can design the hinge region in accordance with the foregoing principles by selection of appropriate codons in the DNA inserted between the nucleotides coding for the leader sequence and the gene encoding the target protein. Cleavage of the expressed fused polypeptide at the built-in cleavage site in the vicinity of the hinge will be increased relative to cleavage of otherwise identical polypeptides which have no hinge. One can further improve and optimize reactivity of the cleavage site by additional empirically directed alterations to the amino acid sequence of the hinge region. Results from computer graphics/molecular dynamic calculations in conjunction with experimental observation of enzyme kinetics using various hinge sequences can often aid in this optimization by suggesting appropriate alterations to the prototype design of the hinge region.

Further disclosure of the nature and properties of the hinge are disclosed in copending patent application Ser. No. 028,404, filed on even date herewith, the disclosure of which is incorporated herein by reference.

The invention is essentially unlimited with respect to the identity of the target protein to be manufactured using the procedures and constructs disclosed herein. Indeed, an important feature of the invention is that it provides a generalized procedure which can be adapted readily to facilitate engineered production of any desired protein. Thus, this invention may be used to produce growth factors, hormones, lymphokines, enzymes, antibodies or their various fragments including binding sites, viral and procaryotic proteins including both enzymatically active and inactive proteins, short polypeptides, and various analogs of all of the above. Nonlimiting examples include EGF, IGF-1, TGF alpha and beta, human collagenase inhibitor, PDGF, CTAP, interleukins, interferons, industrial enzymes, thrombolytic agents, vital envelope proteins, bacterial membrane proteins, protein A and its fragments, and various synthetic peptides.

The following examples more fully illustrate preferred features of the invention.

EXAMPLE

A series of fused polypeptides comprising human epidermal growth factor (EGF) linked to hook polypeptides of various designs were expressed in prokaryotes by transfecting *E. coli* with expression vectors made by inserting DNA encoding the various fused polypeptide products into the BglII, EcoRI, and BamHI sites of plasmid pKK (Amman et al-Pharmacia) modified to promote high copy number and to impart tetracycline resistance; and plasmid pGG, derived from pBr322 and modified to contain the Trp promoter. Each of the transformants were cultured, and about 30 micrograms fusion product per gram of wet cell paste were collected.

Three different pendant polypeptides were designed, all of which comprised a glutamic acid residue immediately adjacent the asparagine residue constituting the amino terminus of the EGF target protein. Polypeptide 1 had a truncated TRP-LE sequence as a leader connected at its carboxyl end, via the glutamic acid residue, to the EGF. It thus contained no engineered hinge region. Polypeptide 2 was designed to have in sequence arginine, aspartic acid, and leucine residues disposed between the truncated TRP-LE leader and a glutamic acid residue as a cleavage site. It was hypothesized that this tripeptide could be useful as a hinge because Asp and Arg are charged residues and therefore might promote relaxation of the section of the fused polypeptide adjacent the cleavage site by increasing its solubility. Peptide 3 included a pendant polypeptide comprising in sequence the truncated TRP-LE followed by 43 residues derived from the TRP leader sequence (which had been modified by conventional techniques to change the endogenous Met residues to Val and the Glu residues to Asp,) Asp-Leu as a hinge, the Glu cleavage site, and the EGF. The amino acid sequences of each of these hook regions are set forth below.

P-1

MET—LYS—ALA—ILE—PHE—VAL—LEU—LYS—GLY—SER—LEU—ASP—<u>GLU</u>—EGF

P-2

MET—LYS—ALA—ILE—PHE—VAL—LEU—LYS—GLY—SER—LEU—ASP—A̅R̅G̅—A̅S̅P̅—L̅E̅U̅—<u>GLU</u>—EGF

P-3
MET—LYS—ALA—ILE—PHE—VAL—LEU—LYS—GLY—SER—LEU—ASP
ARG—ASP—LEU—ASP—SER—ARG—LEU—ASP—LEU—ASP—VAL
ARG—THR—ASP—HIS—LYS—ASP—LEU—SER—ASP—HIS—LEU
VAL—LEU—VAL—ASP—LEU—ALA—ARG—ASN—ASP—LEU—ALA
ARG—ILE—VAL—THR—PRO—GLY—SER—ARG—TYR—VAL

ALA—A̅S̅P̅—L̅E̅U̅—<u>GLU</u>—EFG

The overlined residues constitute the hinge; the underlined residues constitute the primary cleavage site; EGF indicates the known amino acid sequence of human epidermal growth factor; and the remaining residues constitute the leaders.

Figure 3:
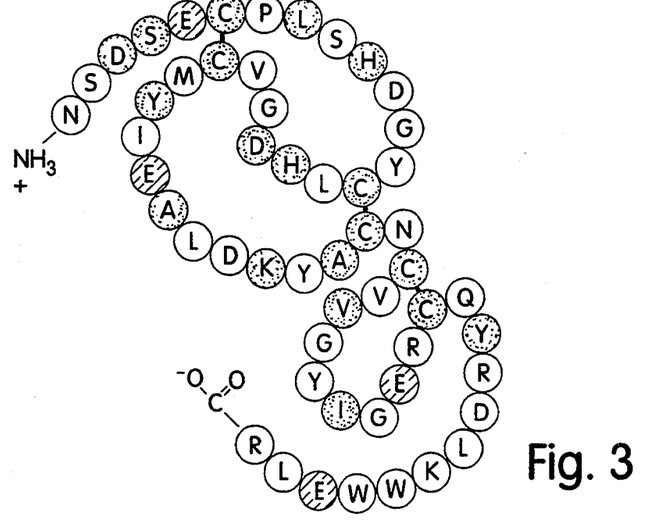
FIG. 3 is a two-dimensional representation of the amino acid structure and conformation of human EGF using the standard one letter code to identify amino acids.

As can be seen from FIG. 3, the 53 amino acid EGF protein contains Glu residues at positions 5, 24, 40, and 51. Previous experiments had indicated that the Glu residues at positions 5, 24, and 40 were not significantly attacked by V-8 protease provided the EGF had been renatured and was held in its native conformation by three disulfide bonds spanning cysteine residues 6-20, 14-31, and 33-42. The Glu residue at position 51, however, was cleaved rather efficiently, resulting in a 51 amino acid EGF analog. The purpose of the design of the foregoing leaders was to produce a fused protein which could be cleaved preferentially at the Glu cleavage site adjacent the EGF. Prior to the addition of the cleavage enzyme, the fused proteins were renatured by dissolving collected inclusion bodies in urea. After approximately 12-16 hours at room temperature, the urea was dialyzed out. If renaturation is omitted, treatment with V-8 protease cleaves at all four Glu residues in the EGF structure.

Each of the fused polypeptide products were subjected to V-8 protease digestion for one hour. V-8 protease (ICN) was added at a concentration of 1% of the fused polypeptide concentration, which was set at about 1.0 mg/ml. The cleavage was conducted at 37° C. in 100 mM ammonium acetate, 1 mM EDTA, pH 8. The cleavage reactions were stopped by decreasing the temperature to 4° C. and by dilution with 20 mM phosphate buffer, pH 7. 50 microliter samples of the reaction mixtures were injected into a C-18 HPLC column (5 micron) previously equilibrated with buffer (82% sodium phosphate, 18% acetonitrile) to resolve the components of the cleavage reactions. Elution was conducted with an 18% to 32% acetonitrile gradient. Protein was detected by absorbance at 214 nm. After 5-10 minutes the cleaved 51 amino acid and 53 amino acid EGFs were detected.

Figure 4:
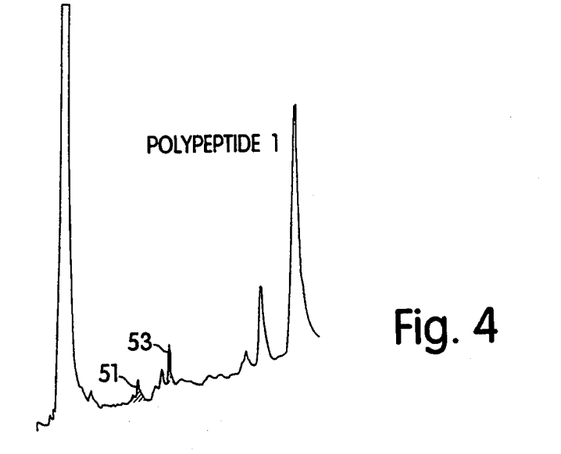
FIGS. 4-6 are graphs showing the relative amounts of 53 to 51 amino acid EGF proteins produced by a one hour cleavage reaction using V-8 protease while varying the nature of the hinge in three fused polypeptides.
Figure 5:
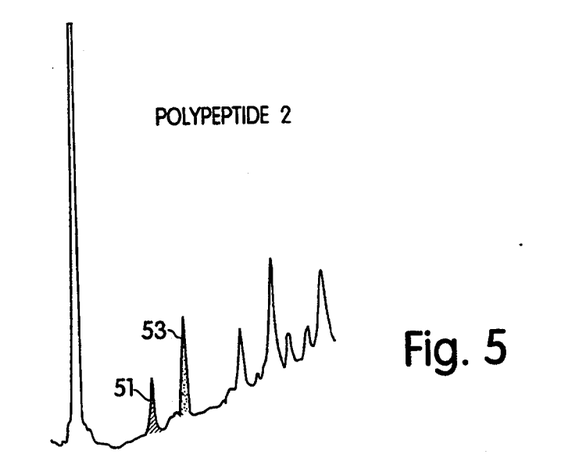
Figure 6:
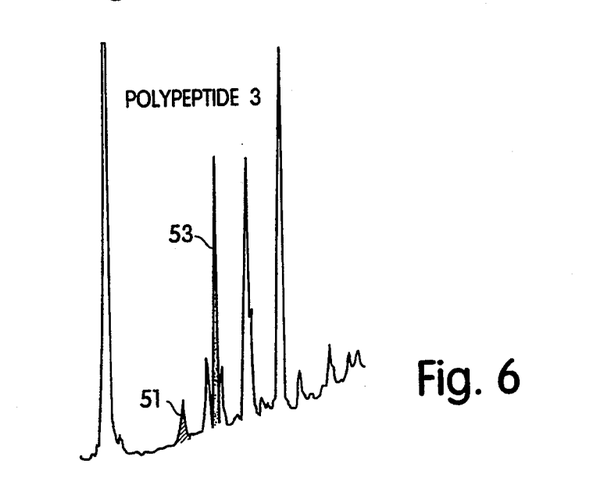

The output of the detector for the three samples is shown in FIGS. 4, 5, and 6. Polypeptide 1 is cleaved at a much slower rate than polypeptide 2 or 3. After 1 hour, more 53 than 51 was produced in all three samples, but cleavage efficiency was increased in the polypeptides containing the hinge regions (2 and 3), and selectivity of cleavage was improved in polypeptide 3. This work illustrates that the relative rate of cleavage at the primary and secondary cleavage sites can be influenced to favor cleavage at the primary site in the pendant polypeptide, and that the inclusion of a hinge promotes such preferential cleavage.

Figure 7:
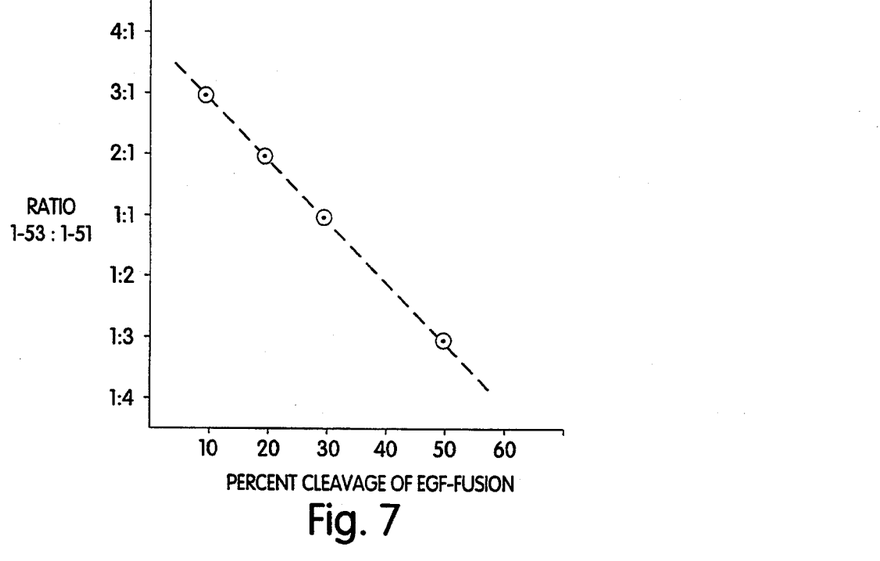
FIG. 7 is a graph of the ratio of 53 to 51 amino acid EGF proteins vs. percent cleavage of EGF fusion protein for a cleavage reaction using V-8 protease which cleaves at the Glu residue adjacent the EGF to produce intact EGF (53 amino acid protein) and at a Glu-51 residue in EGF to produce a 51 amino acid analog of EGF.

It was observed that the ratio of the intact target protein to the truncated analog produced upon cleavage of the secondary cleavage site at position 51 in the EGF target protein decreased as the total amount of fused polypeptide cleaved increased. With respect to polypeptide 3, when 10% of the protein was cleaved, the 53/51 ratio was approximately 3:1, whereas, when 50% of the protein was cleaved, the ratio was about 1:3. The relationship of the 53:51 ratio to percent polypeptide cleaved is shown in FIG. 7. The graph permits determination of the time point when the maximum 53:51 ratio is observed.

Figure 8:
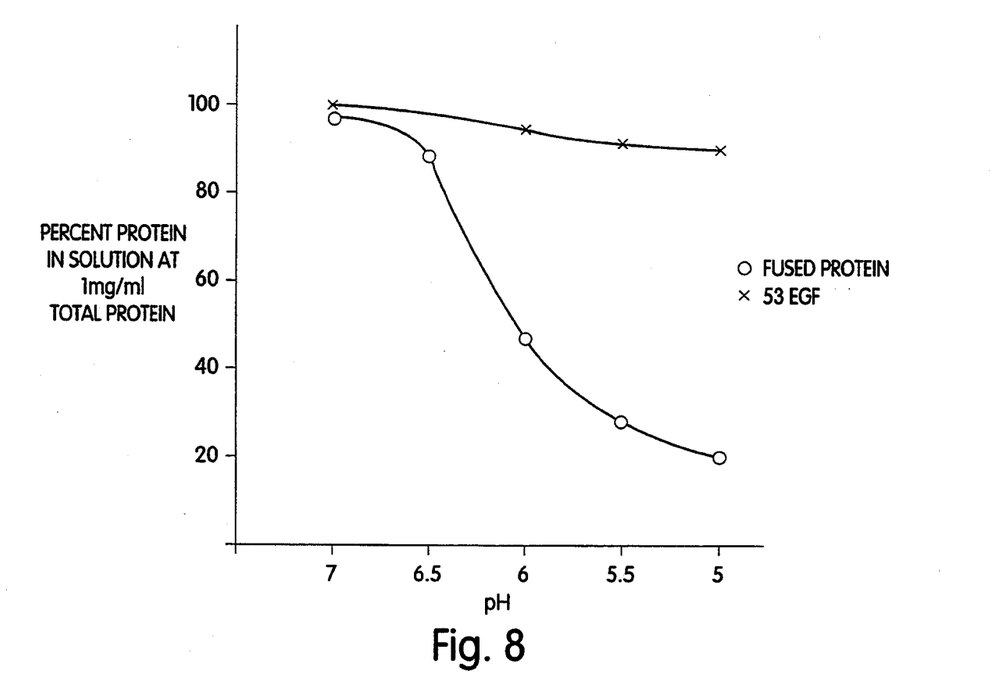
FIG. 8 is a graph of the percent protein in solution vs. pH, illustrating a basis for separating intact EGF from fused protein useful in the recycling method.

The cleavage reaction was conducted at pH 8 as this pH was observed to be optimal. A protein concentration of 1.0 mg/ml of reaction mixture was set by dilution. About 0.27 mg protein were then subjected to V-8 protease digestion under the conditions described above until the monitored concentration ratios of 53:51 optimized. The reaction was stopped at that time by lowering the temperature and adding HCl to lower the pH to 5.5. At this pH, most of the fused polypeptide remaining precipitate, whereas the 53 and 51 EGFs remain soluble, permitting separation by centrifugation (see FIG. 8). The remaining fused product was then resolubilized by suspension at pH 10, resubjected to V-8 protease digestion at pH 8 to produce further cleavage product, and this cycle was repeated a third time. The results of this recycle method are set forth below.

| Cycle | mg total Protein in Supernatant | Micrograms 53 EGF | Micrograms 51 EGF |
|---|---|---|---|
| 1 | .27 | 51 | 16 |
| 2 | .19 | 38 | 30 |
| 3 | .17 | 36 | 34 |
|   |   | 125 | 80 |

In contrast, if the V-8 protease is added and the reaction is simply left to go to completion, no detectable amount of intact 53 amino acid EGF protein is produced.

Figure 9A:
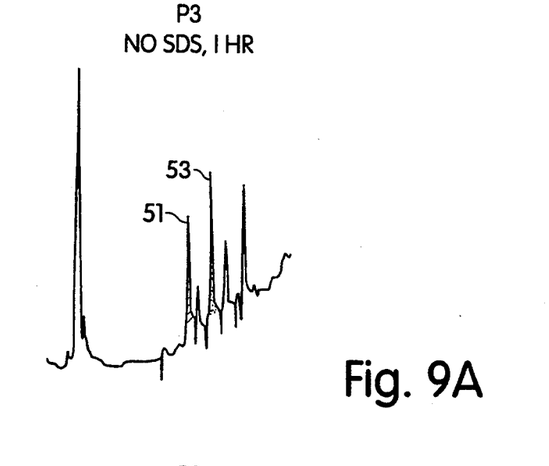
FIGS. 9A, 9B, and 9C are graphs showing the relative amounts of 53 and 51 amino acid EGF proteins in a cleavage reaction system using V-8 protease for 1 hour in the presence and absence of sodium dodecyl sulfate (9A and 9B), and for 3 hours in the presence of sodium dodecyl sulfate (9C)
Figure 9B:
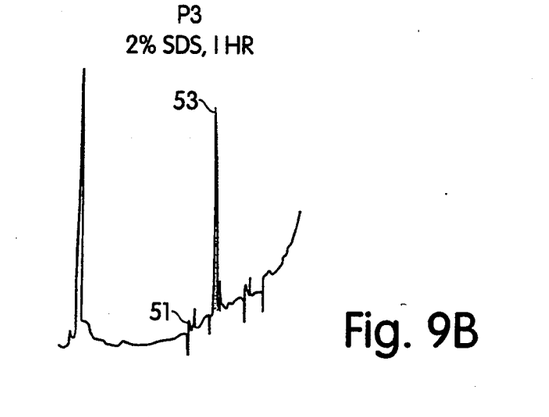
Figure 9C:
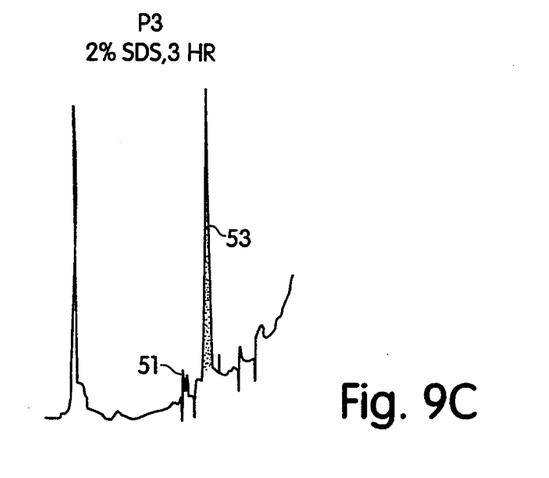

It was discovered that in the presence of sodium dodecyl sulfate, sodium laurate, or N-dodecyl, N-3-propane sulfonic acid, N,N-dimethyl ammonium (Zwitterion 3-12), cleavage to produce 53 amino acid EGF over 51 amino acid EGF was favored further. As shown, for example, in FIGS. 9A and 9B, cleavage of polypeptide 3 for one hour (pH 6.5) in the presence of sodium dodecyl sulfate (2% v/v) greatly increased the rate of cleavage at the primary cleavage site, producing intact 53 amino acid EGF, versus the rate of cleavage at the secondary cleavage site within the target protein, producing the 51 amino acid EGF analog. In fact, as shown in FIG. 9C, in the presence of 2% SDS, after 3 hours of reaction, the ratio of the 53 amino acid EGF to the 51 amino acid EGF is greater than 20:1.

EXAMPLE II

V-8 protease was immobilized on Sepharose 4B (crosslinked polyglucose, Pharmacia) by first dissolving 5 mg of the enzyme in 100 ml of 0.1M sodium bicarbonate at pH 8. The solution was kept on ice. 100 ml of Sepharose CL-4B were washed with 500 ml cold water and then added to 100 ml $H_2O$, adjusted to pH about 11, with sodium hydroxide. This slurry was also kept on ice. The resin was activated by adding 10 g CNBr dissolved in 10 ml $CH_3CN$ while maintaining the pH at 10-11 by additions of NaOH. The reaction was allowed to continue for about 15 minutes until the pH drop slowed considerably. The activated resin was then washed with cold $CH_3CN$ solution (20% $CH_3CN$ in 500 ml $H_2O$) and cold 0.1M sodium bicarbonate.

The protein solution was then added to the resin, and the reaction mixture was rotated for one hour at 4° C., resulting in immobilized active enzyme bound to the beads.

50 ml of the bead matrix was packed into a column, and a solution of polypeptide 3 in 0.1 mM ammonium acetate was passed through the column.

In a first series of experiments, the pH of the buffer solution was varied. Solutions having a pH of 7.0, 7.5, 8.0, 8.5, and 9.0 were tested for cleavage efficiency by passage through the immobilized enzyme columns, and then separating the digestion mixture components by HPLC. It was discovered that 100% cleavage was achieved at pH 8.5, i.e., that optimal pH for cleavage had shifted from 8.0 for enzymes in solution to 8.5 for enzyme immobilized on Sepharose.

Figure 10A:
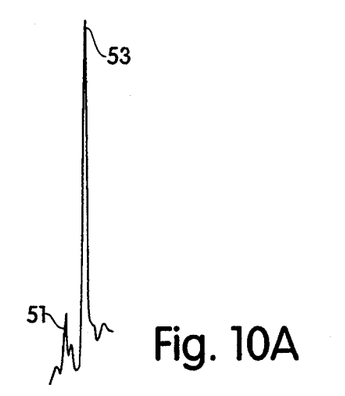
FIGS. 10A, 10B, and 10C are graphs showing the relative amounts of 53 and 51 amino acid EGF proteins in a cleavage reaction system using V-8 protease immobilized on crosslinked polyglucose (Sepharose 4B) illustrating how flow-rate influences the 53:51 ratio.
Figure 10B:
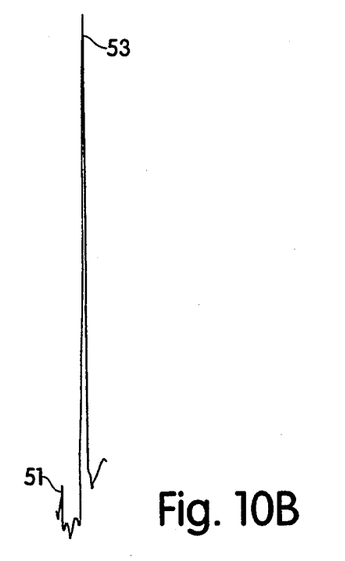
Figure 10C:
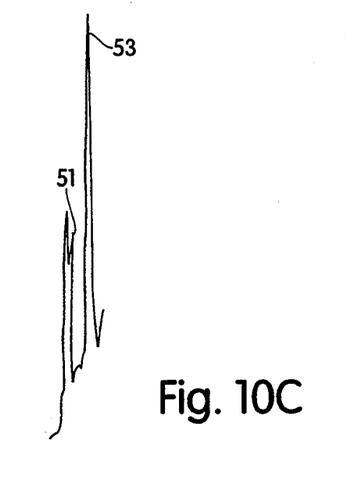

The residence time of reactive contact between the enzyme and substrate was then optimized by passing samples of the fused protein solution through the column at various flow rates. HPLC plots showing the 53:51 EGF cleavage products ratios are set forth in FIGS. 10A, 10B, and 10C. At 7.5 ml/min., cleavage at the primary cleavage site dominated, but insufficient amounts of intact EGF were produced. (See FIG. 10A) At a flow rate of 6.0 ml/min., the amount of 51 amino acid EGF analog produced was essentially identical to the faster flow rate, but significantly more intact, 53 amino acid EGF was produced (See FIG. 10B). At 3.8 ml/min., the ratio of 53:51 decreased significantly, indicating that at this residence time intact EGF was being cleaved at its Glu at position 51, thereby reducing yield (see FIG. 10C).

The invention may be embodied in other specific forms.

What is claimed is:

1. In a process for producing an intact, recombinant, target protein by cleaving a recombinant fused polypeptide, said fused polypeptide comprising a continuous sequence of amino acids defining said target protein, a pendant polypeptide, and a primary cleavage site disposed adjacent to the target protein in the pendant polypeptide, said target protein comprising an amino acid sequence defining a secondary cleavage site, each of said primary and secondary cleavage sites being hydrolyzable by a single selected cleavage agent such that treatment with said selected cleavage agent under cleavage conditions induces hydrolytic cleavage of said fused polypeptide at both said primary and secondary cleavage sites, the improvement wherein the fused polypeptide is treated to yield enhanced quantities of an intact target protein by the steps of:
   A) subjecting the fused polypeptide to said cleavage agent in a reaction mixture under conditions in which the cleavage agent cleaves the fused polypeptide at both the primary and secondary cleavage sites, the rate of cleavage at the primary cleavage site being initially greater than the rate of cleavage at the secondary cleavage site, and the rate of cleavage at the secondary cleavage site approaching the rate of cleavage at the primary cleavage site as the cleavage reaction progresses;
   B) separating cleaved, intact target protein from the reaction mixture of step A prior to completion of the cleavage reaction at said primary cleavage site and prior to the establishment of equilibrium between the rates of cleavage at the primary and secondary cleavage sites, thereby producing intact target protein and a remaining reaction mixture comprising an uncleaved amount of said fused polypeptide; and
   C) subjecting the uncleaved amount of said fused polypeptide in said remaining reaction mixture to the cleavage agent to produce an additional amount of cleaved intact target protein, and a second remaining reaction mixture.

2. The process of claim 1 comprising the additional steps of separating said additional amount of cleaved intact target protein from said second reaction mixture and subjecting said second reaction mixture of step C to the cleavage agent to produce a further amount of cleaved, intact protein.

3. The process of claim 1 comprising the step of renaturing said fused polypeptide prior to step A, and conducting step A under conditions in which the target protein remains in its tertiary conformation during cleavage.

4. The process of claim 3 wherein the target protein comprises multiple Cys residues, and wherein said fused polypeptide is oxidized prior to step A so that the target protein is held in its tertiary conformation during cleavage.

5. The process of claim 1 wherein the cleavage agent and the primary and secondary cleavage sites are selected from the group consisting of the cleavage agents: trypsin, chymotrypsin, elastase, pepsin, papain, subtilisin, thermolysin, V-8 protease, endoproteinase, Arg C, clostripain, thrombim, collagenase, lysobacter, enzymogenese, mysobacter A1-1, protease, armillaria mellea, flavobacterium, meringosepticum, factor Xa, CNBr, BNPS-skatole, N-bromosuccinidine, 0-iodosobenzoic acid, HBr/DMSO, NTCB, sodium metal in liquid ammonia hydroxylamino, and dilute acid.

6. The process of claim 1 wherein said selective cleavage agent is an endopeptidase.

7. The process of claim 6 wherein step A is conducted by immobilizing the endopeptidase on an insoluble support matrix and passing a solution of the fused polypeptide over the support matrix.

8. The process of claim 1 wherein step A is conducted in an aqueous solution having a pH which favors cleavage at the primary cleavage site.

9. The process of claim 1 wherein the primary and secondary cleavage sites comprise the same amino acid or amino acid sequence.

10. The process of claim 1 wherein the target protein is EGF.

11. The process of claim 1 wherein the primary and secondary cleavage sites comprise a glutamic acid residue, and the cleavage agent is $S.$ $aureus$ V-8 protease.

12. The process of claim 11 wherein the target protein is EGF.

13. The process of claim 11 or 12 wherein step A is conducted in the presence of a charged organic molecule.

14. The process of claim 11 or 12 wherein step A is conducted in the presence of an organic molecule having 12 carbon atoms attached to a charged moiety.

15. The process of claim 14 wherein said charged organic molecule is selected from the group consisting of dodecyl sulfate salt, a lauric acid salt, and an N-dodecyl, N-lower alkyl sulfonic acid quaternary ammonium zwitterion.

16. The process of claim 1 wherein the target protein is human EGF, the primary and secondary cleavage sites comprise glutamic acid residues, the cleavage agent comprises $S.$ $aureus$ V-8 protease, and step A is conducted in the presence of a charged organic molecule which inhibits cleavage of a glutamic acid residue in said EGF.

17. The process of claim 16 wherein the $S.$ $aureus$ V-8 protease is immobilized on a solid support during step A.

18. The process of claim 16 wherein step A is conducted under conditions during cleavage in which the EGF is disposed in its tertiary conformation.

19. The process of claim 1 wherein said separation step is conducted by altering the properties of the reaction mixture to insolubilize one of said fused protein and said target polypeptide, and separating a supernatant from a precipitate.

20. A process for cleaving a fused, recombinant polypeptide to obtain intact EGF, said fused polypeptide comprising
   EGF having a Glu residue at position 51 and
   a pendant polypeptide having a Glu residue adjacent said EGF, said process comprising the step of treating said fused polypeptide with *S. aureus* V-8 protease in a reaction mixture containing a charged organic molecule under conditions in which the *S. aureus* V-8 protease cleaves said fused polypeptide at the Glu residue adjacent the EGF preferentially to the Glu residue at EGF position 51.

21. The process of claim 20 wherein said charged organic molecule is selected from the group consisting of dodecyl sulfate salt, a lauric acid salt, and an N-dodecyl, N-lower alkyl sulfonic acid quaternary ammonium zwitterion.

22. The process of claim 20 wherein said charged organic molecule comprises 12 carbon atoms and an anionic moiety.

23. The process of claim 20 wherein the treatment step is conducted while the fused polypeptide is disposed in its tertiary conformation.

24. A method of producing an intact, recombinant target protein by cleaving a recombinant fused polypeptide, said fused polypeptide comprising a continuous sequence of amino acids defining said target protein, a pendant polypeptide, and a primary cleavage site disposed adjacent the target protein hydrolyzable by a selected endopeptidase, said target protein comprising a secondary cleavage site each of said primary and secondary cleavage sites being hydrolyzable by said selected endopeptidase, the initial rate of cleavage at said primary site exceeding the initial rate of cleavage at said secondary site under cleavage conditions, said method comprising the steps of:

A. immobilizing said selected endopeptidase on the exposed surface of an insoluble support matrix;
B. passing an aqueous solution of said fused polypeptide over said matrix in reactive contact with the immobilized endopeptidase;
C. controlling the time the fused polypeptide solution is in reactive contact with said immobilized cleavage agent so as to prevent the establishment of equilibrium between the rates of cleavage at said primary and secondary sites, such that said fused polypeptide is cleaved preferentially at said primary cleavage site, producing intact target protein and a remaining reaction mixture; and
D. separating said target protein from the remaining reaction mixture.

25. The method of claim 24 wherein said fused polypeptide is renatured prior to step B, and step B is conducted under conditions in which said target protein remains in its tertiary conformation during cleavage.

26. The method of claim 24 wherein said primary cleavage site is a Glu residue and said endopeptidase is *S. aureus* V-8 protease.

27. The method of claim 24 or 26 wherein said target protein is EGF.

28. The method of claim 24 wherein said insoluble support matrix comprises cross-linked polyglucose.

29. The method of claim 24 wherein said insoluble support matrix comprises a polyvinylidine fluoride surface.

* * * * *